(12) United States Patent
Lazarowich

(10) Patent No.: US 10,561,184 B2
(45) Date of Patent: Feb. 18, 2020

(54) PROTECTIVE COMPOSITE FABRIC

(71) Applicant: Linda Lazarowich, Winnipeg (CA)

(72) Inventor: Linda Lazarowich, Winnipeg (CA)

( * ) Notice: Subject to any disclaimer, the term of this patent is extended or adjusted under 35 U.S.C. 154(b) by 1010 days.

(21) Appl. No.: 14/262,736

(22) Filed: Apr. 26, 2014

(65) Prior Publication Data
US 2015/0282761 A1 Oct. 8, 2015

Related U.S. Application Data

(63) Continuation of application No. 12/923,265, filed on Sep. 13, 2010, now abandoned.

(51) Int. Cl.
| | |
|---|---|
| *F41H 1/02* | (2006.01) |
| *A41D 31/24* | (2019.01) |
| *F41H 5/02* | (2006.01) |
| *A41D 13/00* | (2006.01) |
| *A61F 7/10* | (2006.01) |
| *B32B 3/16* | (2006.01) |
| *B32B 5/02* | (2006.01) |
| *D04H 1/4374* | (2012.01) |

(52) U.S. Cl.
CPC ....... *A41D 31/245* (2019.02); *A41D 13/0012* (2013.01); *A61F 7/10* (2013.01); *B32B 3/16* (2013.01); *B32B 5/024* (2013.01); *D04H 1/4374* (2013.01); *F41H 1/02* (2013.01); *F41H 5/02* (2013.01); *B32B 2307/581* (2013.01); *B32B 2571/02* (2013.01)

(58) Field of Classification Search
None
See application file for complete search history.

(56) References Cited

U.S. PATENT DOCUMENTS

| 6,035,438 A * | 3/2000 | Neal | B32B 3/06 |
| | | | 2/2.5 |
| 6,349,201 B1 * | 2/2002 | Ford | F41H 1/02 |
| | | | 2/455 |
| 7,805,767 B2 * | 10/2010 | McElroy | F41H 1/02 |
| | | | 2/2.5 |

(Continued)

OTHER PUBLICATIONS https://patents.google.com/patent/RU2229087C1/en?q=fish&q=scale&q=armor&q=fabric&oq=fish+scale+armor+fabric (Year: 2002).*

(Continued)

*Primary Examiner* — Arti Singh-Pandey
(74) *Attorney, Agent, or Firm* — Hovey Williams LLP

(57) ABSTRACT

The invention relates to a slash and gash resistant protective composite fabric comprising at least one layer of base fabric, wherein the base fabric is a densely woven, ballistic fabric. At least one layer of rigid fabric, each having a base layer and a hard polymer layer having a special matrix, is bonded onto the base layer, and the rigid fabric is cut into strips of material having a scale-like pattern or shape. Each of the strips of material are connected to the layer of base fabric in overlapping layers whereby the base fabric is covered. The protective composite fabric further includes a resilient elastically deformable material having at least one sensor therein for monitoring of vital signs of a wearer, the resilient elastically deformable material being connected with the at least one layer of a base fabric and the rigid fabric.

16 Claims, 5 Drawing Sheets

(56) References Cited

U.S. PATENT DOCUMENTS

| | | | | |
|---|---|---|---|---|
| 8,069,768 | B2* | 12/2011 | Neal | B32B 3/06 |
| | | | | 89/36.01 |
| 8,291,808 | B2* | 10/2012 | Howland | B32B 3/16 |
| | | | | 2/2.5 |
| 8,434,396 | B1* | 5/2013 | Wiley | F41H 1/02 |
| | | | | 2/2.5 |
| 2007/0260407 | A1* | 11/2007 | Van Albert | A61B 5/6805 |
| | | | | 702/57 |

OTHER PUBLICATIONS https://institutions.newscientist.com/article/mg21729016-000-body-armour-to-scale-up-by-mimicking-flexible-fish/ no date.*
https://www.popularmechanics.com/science/a12086/4275401/ no date.*
https://patents.google.com/scholar/13619310661876592838?q=fish&q=scale&q=armor&q=fabric&scholar&oq=fish+scale+armor+fabric (Year: 2014).*

* cited by examiner

PROTECTIVE COMPOSITE FABRIC

This invention relates generally to a protective composite fabric, and more particularly to an improved slash and gash resistant protective composite fabric, for use with humans and animals, in the manufacture of protective garments which are lightweight, durable and reliable, and which can provide protection of body parts in addition to the chest/torso region, such as arms and legs, and which has a resilient elastically deformable material having at least one sensor therein for monitoring of vital signs of a wearer.

DESCRIPTION OF THE PRIOR ART

It is well known that various stab resistant articles or garments, such as ballistic vests, have been worn by prison corrections officers and other types of security, military or law enforcement personnel, and have even been developed for working animals such as dogs or horses. Such stab resistant articles are designed to prevent bodily penetration as a result of stabbing or slashing from sharp objects or weapons. Unfortunately, these protective articles were generally rigid shields which were externally worn and were constructed of heavy, bulky and inflexible metal components such as titanium or other extremely hard metal alloys. The metallic composition of these cumbersome external vest shields must be of sufficient thickness, rigidity and strength to stop impacts imparted by an attacker.

Disadvantageously, the bulk and rigidity of such metallic vest garments rendered it uncomfortable to wear. Furthermore, it is rather difficult for the wearer of a rigid vest to move and maneuver around quickly and easily which is important especially if the wearer is being attacked. Accordingly, such known puncture resistant articles often prove to be ineffective predominantly due to the fact that the potential wearer prefers not to wear the bulky torso shield, rather than tolerating its discomfort, as when used for extended periods such items can be hot and heavy.

Another, and perhaps a more significant problem with such types of rigid metallic alloy puncture resistant vests, is that they were not concealable. These known cumbersome shield vests were almost exclusively externally worn and even if they were not worn externally, the bulky nature of such articles make it obvious to a would be attacker that the wearer (corrections officer, etc.) is wearing a protective puncture or stab resistant metallic shield vest. Since the worn vest article cannot be concealed the potential attacker is more prone to stab or slash at a vital area away from the vest such as the lower abdomen, groin, neck or head area. Not only is any element of surprise on the part of the wearer removed by the unconcealed nature of such cumbersome rigid vests, it is highly impractical if not impossible for the undercover personnel to wear such bulky items, and even if used these items offer little to no protection of other body parts such as the arms and legs, damage to which can and do cause severe, life threatening wounds. For example, wounds to the femoral artery can and often kill the person, because there is no protective gear for this area.

Moreover, protective devices, such as vests, do exist for working animals, such as dogs, but these tend to be heavy. Ballistic vests are currently the only garment available to protect against ballistic and sharp objects, and a ballistic vest can weigh from 15-20 pounds. For a working dog of 80-125 pounds, such a ballistic vest is equivalent to roughly 20% of that animal's body weight and wearing such a heavy item can increase the body temperature of the animal or wearer. In hot climates, for example, working dogs can easily overheat and expire when their body temperature increases 3-5 degrees, a risk which is enhanced if conventional ballistic vests are utilized. In some cases, dogs have refuse to move when wearing this heavy gear. As such it would be beneficial to monitor the vital signs of the wearer, whether it be a working animal, such as a dog, to a person wearing the material. Particularly in the case of a working animal, an ideal protective composite fabric would be one the animal would wear around the chest or neck, as part of a uniform or single unit. The animal would be able to move about freely and without cumbersome cables, and, when the animal is nearing a dangerous level for any of the vitals being monitored, the handler or keeper or central station would be alerted to attend to the animal that is under stress before the animal's health is compromised or expiration occurs.

Thus, there is a need to provide a light weight, flexible protective composite fabric which is durable, and which can provide protection to vulnerable body parts of humans and working animals, and which can be removed quickly and easily. There is a further need for a flexible protective composite fabric which can provide protection of body parts, in addition to the chest/torso region, such as arms and legs, and which has a resilient elastically deformable material in association therewith having at least one sensor therein for monitoring of vital signs of a wearer. Furthermore, it would be beneficial to have a protective composite fabric which can provide a built in "Cooling Pack" that helps lower body temperature for animals and humans. In this regard, the present invention substantially fulfills this need.

SUMMARY OF THE INVENTION

It is an object and advantage of the present invention to provide an improved slash and gash resistant protective composite fabric which is light weight, durable, and which can provide protection to vulnerable body parts of humans and working animals, and which can be removed quickly and easily.

It is another object and advantage of the present invention to provide an improved slash and gash resistant flexible protective composite fabric which can provide protection of body parts in addition to the chest/torso region, such as arms, legs and neck, and which has a resilient elastically deformable material in association therewith having at least one sensor therein for monitoring of vital signs of a wearer.

It is another object and advantage of the present invention to provide an improved slash and gash resistant protective composite fabric which can provide a built in "Cooling Pack" that helps lower body temperature for animals and humans.

According to one aspect of the present invention, there is provided a protective composite fabric comprising a) at least one layer of base fabric, wherein the base fabric is a densely woven, ballistic fabric; b) a rigid ballistic fabric having a base layer and a hard polymer layer having a special matrix bonded onto the base layer, the rigid fabric being cut into strips of material having a scale-like pattern or shape and being connected to the at least one layer of base fabric in overlapping layers whereby the at least one layer of base fabric is covered; and c) a resilient elastically deformable material having at least one sensor therein for monitoring of vital signs of a wearer, the resilient elastically deformable material being in association with the at least one layer of a base fabric and the rigid ballistic fabric.

According to another aspect of the present invention, there is provided a system for providing a protective composite fabric comprising providing at least one layer of base fabric, wherein the base fabric is a densely woven, ballistic fabric; providing a plurality of overlapping layers of rigid ballistic fabric connected to the at least one layer of base fabric, the rigid fabric comprising a base layer and a hard polymer layer having a special matrix, the hard polymer layer being bonded onto the base layer; providing a resilient elastically deformable material having at least one sensor therein for monitoring of vital signs of a wearer, the resilient elastically deformable material being in association with the at least one layer of a base fabric and the rigid fabric; cutting the rigid fabric into strips of material; cutting each of the strips of material into a scale-like pattern or shape; and connecting the strips of material to the at least one layer of base fabric in overlapping layers whereby the at least one layer of base fabric is covered.

According to a further aspect of the present invention, there is provided a slash resistant fabric composition comprising at least one inside fabric layer, the at least one fabric layer being constructed and arranged for contact adjacent to the skin or body of a wearer; a first layer and a second layer of aramid fabric; at least one protective composite fabric layer as defined in any one of claims 1 to 5, the at least one protective composite fabric layer being positioned and secured between the first layer and the second layer of ballistic fabric; and at least one outside fabric layer, the at least one outside fabric layer being constructed and arranged to form an outside surface of the slash resistant fabric composition, and wherein the first layer of ballistic fabric, the at least one protective composite fabric layer and the second layer of ballistic fabric are secured and positioned between the at least one inside fabric layer and the at least one outside fabric layer.

BRIEF DESCRIPTION OF THE DRAWINGS

A preferred embodiment of the present invention is described below with reference to the accompanying drawings, in which.

DESCRIPTION OF THE PREFERRED EMBODIMENT

Figure 1:
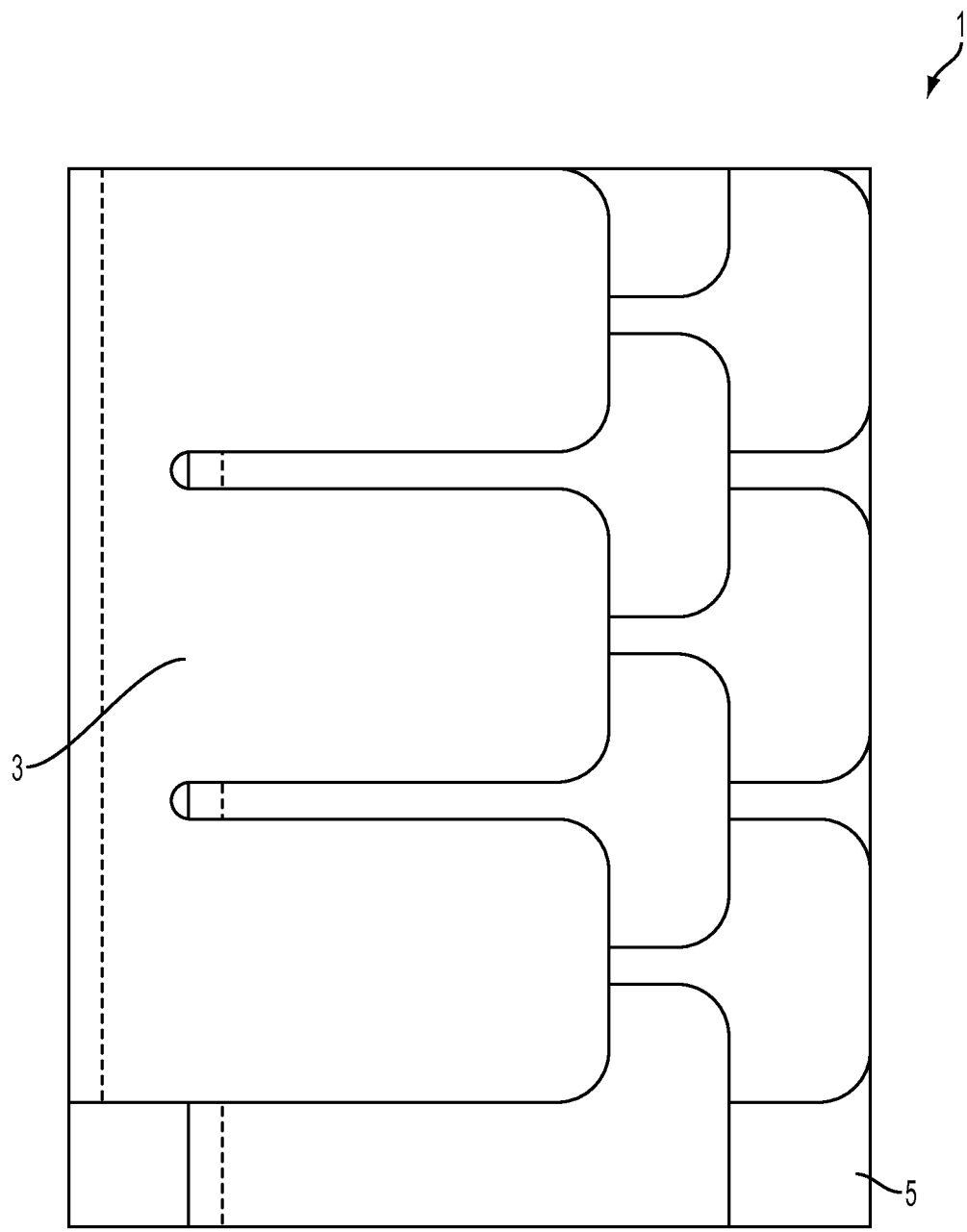
FIG. 1 is a perspective view of an embodiment of the protective composite fabric of the present invention.

In the preferred embodiment, and with reference to FIG. 1, the improved slash and gash resistant protective composite fabric of the present invention is designated in its entirety by the reference numeral 1. The protective composite fabric preferably comprises at least one layer of base fabric 5, wherein the base fabric is a densely woven, ballistic fabric. Two possible examples of materials that could be utilized are Microflex™, manufactured by Teijin, and Kevlar Correctional™, manufactured by Dupont, though other variations to this are possible also, as would be apparent to one skilled in the art.

At least one layer of rigid fabric 3 having a base layer (not shown) and a hard polymer layer (not shown) having a special matrix bonded onto the base layer, is connected onto the base layer, the rigid fabric 3 being cut into strips of material having a scale-like pattern or shape, as shown in FIG. 1, and being connected to the at least one layer of base fabric 5 in overlapping layers whereby the at least one layer of base fabric 5 is substantially covered. Possible examples of suitable materials that could be utilized are SRM™, manufactured by Teijin, and Argus™, manufactured by Dupont, though other variations to this are possible also, as would be apparent to one skilled in the art. It will also be understood that the rigid fabric layer can also comprise a plurality of rigid fabric layers.

In essence, the base fabric 5 is a densely woven, ballistic fabric which has a soft, supple hand, it being understood that "hand" is a textile term for the feel of a fabric, yet which is dimensionally stable and possessing modest stretch when cut on the bias. The rigid fabric 3 is connected to the base fabric 5, preferably by sewing, the rigid fabric 5 being of a type that is effective for protection against sharp objects and weapons.

The rigid fabric 3 is, as noted previously, preferably comprised of two layers; a base layer on to which has been bonded particles of a hard polymer using a special matrix which produces a rigid outer skin. When worn conventionally, it is known that fabrics of this type are effective for protection against sharp edges, but such conventional configurations have also been known to be rigid, uncomfortable, do not bend with the body and can be worn only on large, flat surfaces on the body such as the chest and back. It also does not conform to body contours, which can cause binding, chafing, and generally being uncomfortable to wear other than as a traditional ballistic vest. Both fabrics are light weight, extremely strong, durable but do not easily breath and can cause over-heating of the wearer when worn for extended periods. However, in the present invention, as noted previously, the at least one layer of rigid fabric 3 is cut into strips of material having a scale-like pattern or shape, as shown in FIG. 1, and are then connected to the at least one layer of base fabric 5 in overlapping layers whereby the base fabric 5 is substantially covered. It will, of course, be understood that the strips of material of the rigid fabric 3 could also be cut into various other patterns or shapes that are then overlapped, the overlapping of the material being varied upon depending upon the desired density and protection sought. In this manner, garments utilizing the improved protective composite fabric of the present invention, such as vests or other types of protective articles, are assembled in a unique way that allows for greater flexibility of the fabric and greater maneuverability of the person or animal wearing the garment.

Furthermore, utilizing both fabrics (base fabric 5 that is a densely woven, ballistic fabric having a soft, supple hand in combination with rigid fabric 3) as a single fabric, allows for the incorporation of the best properties of each to create a new, composite fabric with additional new features not otherwise available. In the present invention, the soft, base fabric 5, which can be of a conventional type, is essentially unchanged. The rigid top layer fabric 3, however, is drastically altered in the present invention so as to make it pliable and follow the contours of small body parts in both animal and humans.

The method used to manufacture the improved protective composite fabric of the present invention is as follows:
(A) cutting the rigid fabric 3 into narrow strips;
(B) cutting each strip of the rigid fabric into a scale-like (or other) pattern;
(C) one side of the pre-cut strips of the rigid fabric is sewn to the base fabric 5 in overlapping layers, similar to the application of shingles to a roof. This creates a new protective composite fabric that incorporates both the soft fabric as a base and rigid fabric 3 as overlapping scales that completely covers the base fabric 5.

It should be noted that the scale-like patterns of rigid fabric material can be cut into different widths and lengths to form protective articles which can be manufactured utilizing the improved protective composite fabric of the present invention, depending on the body parts to be protected. For example, it will be understood that the thigh and leg regions of a wearer require a larger scale or pattern size on a formed protective article than that of garments covering the arm and neck. This new composite fabric is a flexible, non-binding, slash and gash resistant fabric which can be used, for example, in law enforcement, military and related applications that require protection against sharp edge weapons, chain and barb wire, brush, burr and cactus and punctures sustained during movement in transit (for horses), shrapnel, and other related hazards.

One further embodiment of the present invention includes, because over-heating is a major concern for animals and humans wearing ballistic gear formed from protective articles or garments (which can be manufactured utilizing the improved protective composite fabric of the present invention), a built in "Cool Pack" (not shown) that helps lower body temperature for the wearer, the "Cool Pack" being positioned within at least one pocket formed on an inner surface of the protective article or garment. Preferably, these "Cool Packs" are rechargeable, lightweight and fit into specially designed pockets on the inside of the garment, next to the body. Other variations to this are possible also, as would be apparent to one skilled in the art. In a preferred embodiment, the "cooling pack" is a re-hydrating cooling gel that can be chilled, or frozen, as needed prior to placement into the pockets on the inside of the garment. In a further embodiment, the garment further comprises a plurality of pockets formed on the inner surface thereof, each operably able to receive the "Cool Packs" therein.

In a still further embodiment, the improved slash and gash resistant protective composite fabric of the present invention can be manufactured and constructed to comprise a kennel, which can possess the above-noted pockets on the inside of the garment whereby the "Cool Packs" can be positioned therein to cool the dog while resting in the kennel, or used on the ground for the dog to stand on it, used to cool the dog's paws. This embodiment can be constructed having 3 layers of fabric as follows: 1) a base fabric, such as nylon, that is placed next to the kennel floor or the ground; 2) a layer of insulation to prevent the heat from the kennel floor or ground from migrating to the cool pack layer; and 3) an upper layer with cool pack pockets to hold the hydrated cool pack inserts. Such and embodiment can be rolled and secured with hook/loop (Velcro) and strap to carry and for storage.

In a still further embodiment, the improved slash and gash resistant protective composite fabric of the present invention can be manufactured and constructed to comprise a dog boot insoles, which slide into existing dog boots that are commercially available on the market. This embodiment would also feature the above-noted pockets on the inside of the garment whereby the "Cool Packs" can be positioned therein. In this embodiment, the improved slash and gash resistant protective composite fabric of the present invention is cut into the shape of the dog boot base, roughly an oval shape, and the insole is made using one or more layers of the slash resistant fabric which are sewn together to prevent slippage/moving; the "insole" is inserted into the dog boot with the polymer matrix/abrasive side down; the dog's foot is then slid into the boot and secured in place with existing boot ties.

Figure 2:
FIG. 2 is a perspective view of an embodiment of the resilient elastically deformable material having at least one sensor therein for monitoring of vital signs of a wearer for use in the protective composite fabric of the present invention.
Figure 3:
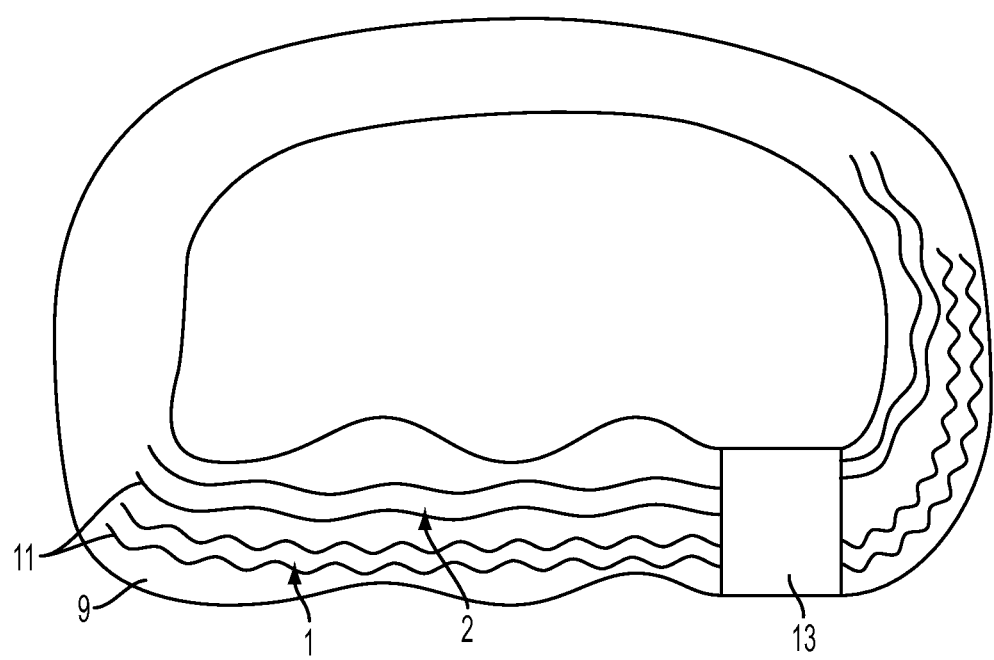
FIG. 3 is a perspective view of another embodiment of the resilient elastically deformable material having at least one sensor therein for monitoring of vital signs of a wearer for use in the protective composite fabric of the present invention.

In a preferred embodiment, the improved protective composite fabric of the present invention further comprises, with reference to FIG. 2, a resilient elastically deformable material 7 having at least one sensor therein for monitoring of vital signs of a wearer, the resilient elastically deformable material 7 being in association with the at least one layer of a base fabric and the at least one layer of the rigid fabric. One possible example of a material that could be utilized is "Life Shirt"™ by Vivometrics, which utilizes an elastic at the top (which is connected to a computer chip) and a band positioned around the wearer's body to monitor vital signs, though other variations to this are possible also, as would be apparent to one skilled in the art. It will be understood that the protective composite fabric of the present invention could further comprise a micro chip computer (not shown) for monitoring the vital signs of the wearer, and that such vital signs of the wearer can be transmitted as a signal sent from a transmitter (not shown) to a receiver (not shown) remote from the protective composite fabric. Of course, such a transmitter could be positioned within the garment, as would be apparent to one skilled in the art. In this manner, and particularly when an animal is wearing the garment, when the animal is nearing a dangerous level for any of the vitals being monitored, the handler or keeper or central station would be alerted to attend to the animal that is under stress before the animal's health is compromised or expiration occurs.

Figure 4:
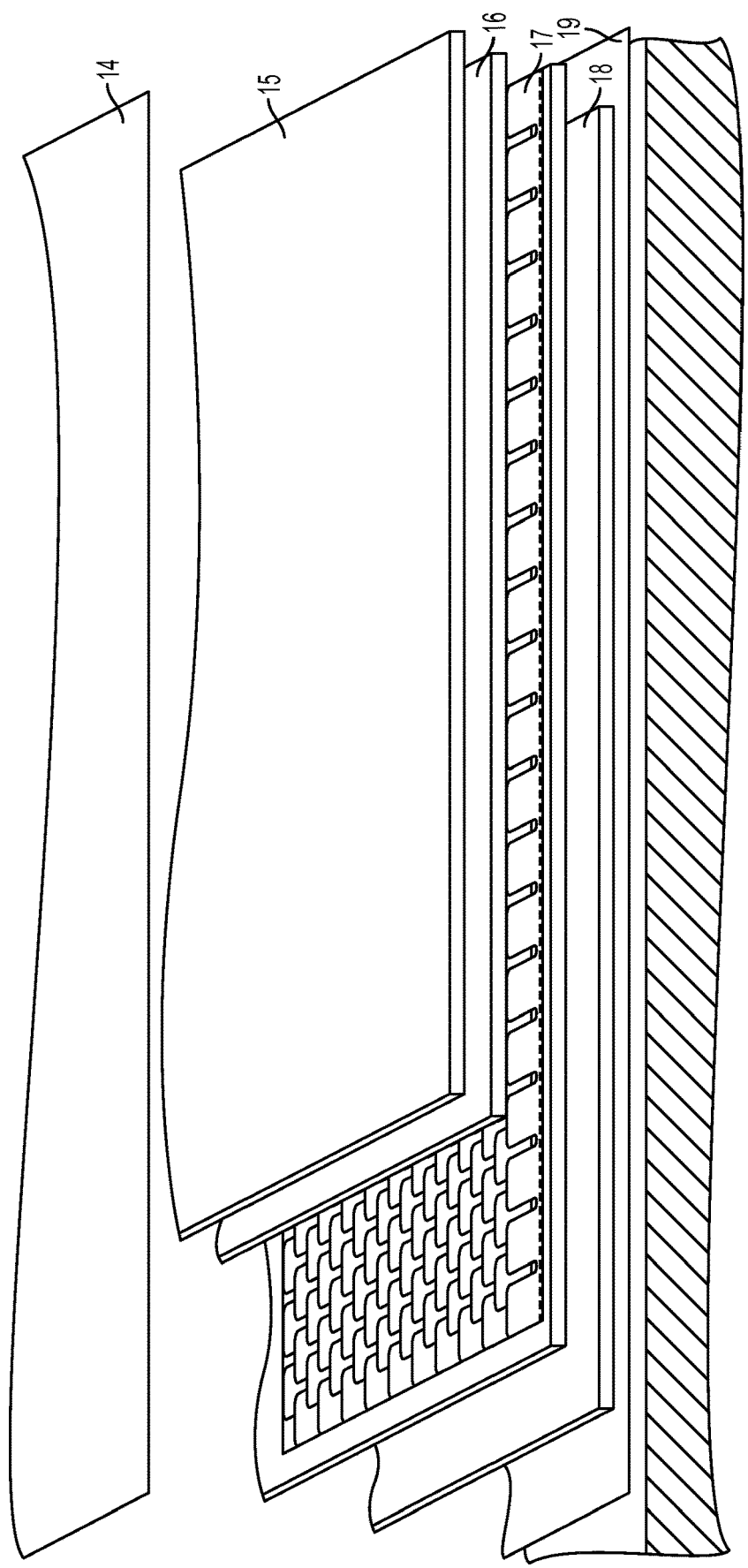
FIG. 4 is an exploded view of an embodiment of the protective composite fabric of the present invention sandwiched between inner and outer layers of fabric to form a protective garment.
Figure 5:
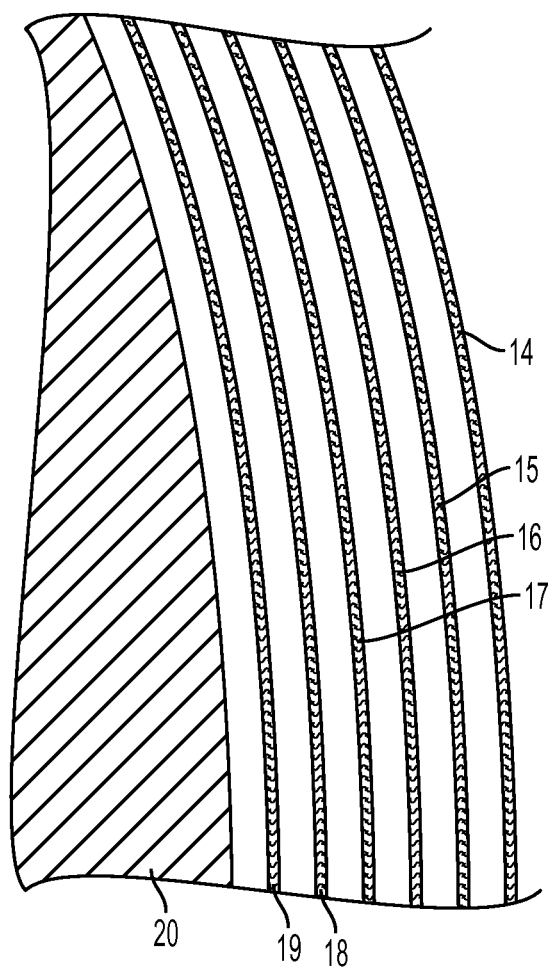
FIG. 5 is a side view of an embodiment of the protective composite fabric of the present invention sandwiched between inner and outer layers of fabric to form a protective garment.

With reference to FIGS. 4 and 5, protective articles can be manufactured utilizing the improved protective composite fabric of the present invention. Examples of such protective gear designed for the human body in law enforcement or for military and security personnel, are gauntlets (Flexi-Shield from wrist to elbow and wrist to upper arm), gaiters (Flexi-Shield ankle to knee), foot guards (Flexi-Shield worn under stockings and in shoes), palm and thumb guards (Flexi-Shield worn under leather gloves), neck guards, groin guards (Flexi-Shield to protect femoral artery, inner thigh area in the groin/pelvic area; worn over or under work pants, wind suits with Flexi Shield in arms, legs and groin area, coveralls or chaps.

Protective articles can also be manufactured for working dogs, horses or other animals utilizing the improved protective composite fabric of the present invention. Examples of such can be blankets, leg guards with flexi-shield to protect against sharp edges, barb wire, etc., or a full body uniform with flexi-shield reinforcement for coverage of the belly, sides, spine and neck, possibly in conjunction with the previously noted Cool Pack technology, or partial body coverage for one or a combination of chest, under belly or other areas such as neck region. In such configurations the present invention provides less weight for the wearer to wear, in that the weight of a protective garment made with the composite fabric of the present invention can have a weight of approximately 1.5 lbs versus that of 20 lb for a conventional ballistic vest.

FIGS. 4 and 5 illustrate embodiments of the layering of fabric layers that can be assembled and manufactured to form protective, slash resistant articles utilizing the improved protective composite fabric of the present invention therein. The skin (body) of a human or animal (such a dog or horse) is illustrated as 20 in FIG. 4. In a preferred embodiment, an embodiment of the protective composite fabric 17 of the present invention is sandwiched between at least one or more layers of yellow fabric 16 and 18, it being understood that either of yellow fabric layers 16 and 18 may each comprise multiple layers of yellow fabric, these preferably being yellow aramid fabric layers. These yellow fabric layers 16 and 18 (which obviously have the protective composite fabric 17 positioned therebetween) are then in turn encased between each of an inside layer 19 of covering fabric, and an outside layer 15 of covering fabric, which, of course are all sewn or secured together around the edges. In a preferred embodiment, this inside layer 19 is positioned immediately adjacent to the skin or body 20 of the wearer (as shown in FIG. 4), and the outside layer 15 will form the outer surface of the protective article formed from layering the above-noted fabric layers as described. In a further embodiment, the inside layer 19 of covering fabric may be dispensed with, thus leaving yellow fabric layer 18 positioned immediately adjacent to the skin or body 20 of the wearer. In another preferred embodiment, inside layer 19 and outside layer 15 are formed from black or camouflage covering fabrics.

The present invention has been described herein with regard to preferred embodiments. However, it will be obvious to persons skilled in the art that a number of variations and modifications can be made without departing from the scope of the invention as described herein.

The embodiments of the invention in which an exclusive property or privilege is claimed are defined as follows:

1. A slash resistant protective composite fabric comprising
   at least one first layer and at least one second layer of ballistic and/or slash resistant fabric,
   the at least one first layer abutting the at least one second layer in overlapping relationship,
   the at least one second layer comprising a strip of fabric having a plurality of scale-like members extending therefrom,
   each of the scale-like members being separated from at least one adjacent scale-like member by a through-cut permitting each scale-like member to be independently flexed relative to the other scale-like members while remaining attached to the strip.

2. The protective composite fabric of claim 1, wherein the composite comprises a plurality of the second layers of ballistic and/or slash resistant fabric comprising strips of fabric having the plurality of scale-like members extending therefrom, each of the strips of fabric overlapping an adjacent strip of fabric such that a through cut of one strip at least partially overlies a scale-like member of the adjacent strip.

3. The protective composite fabric of claim 1, wherein the composite further comprises at least one first aramid fabric layer and at least one second aramid fabric layer having the at least one first layer of ballistic and/or slash resistant fabric and the at least one second layer of ballistic and/or slash resistant fabric being positioned and secured therebetween.

4. The protective composite fabric of claim 3, wherein the at least one first aramid fabric layer and the at least one second aramid fabric layer each comprise a plurality of layers of aramid fabric.

5. The protective composite fabric of claim 3, further comprising at least one inside fabric layer positioned adjacent the at least one first aramid fabric layer and being constructed and arranged for contact adjacent a body of a wearer.

6. The protective composite fabric of claim 5, further comprising at least one outside fabric layer being constructed and arranged to form an outside surface of the protective composite fabric, and wherein the at least one first aramid fabric layer, the at least one first layer of ballistic and/or slash resistant fabric, the at least one second layer of ballistic and/or slash resistant fabric, and the at least one second aramid fabric layer are secured and positioned between the at least one inside fabric layer and the at least one outside fabric layer.

7. The protective composite fabric of claim 1, further comprising a resilient elastically deformable material being in association with the at least one first layer of ballistic and/or slash resistant fabric layer and the at least one second layer of ballistic and/or slash resistant fabric and having at least one sensor therein for monitoring of vital signs of a wearer.

8. The protective composite fabric of claim 7, further comprising a micro-chip computer for monitoring the vital signs of the wearer.

9. The protective composite fabric of claim 7, wherein the vital signs of the wearer are transmitted as a signal sent from a transmitter to a receiver remote from the protective composite fabric.

10. The protective composite fabric of claim 1, further comprising at least one pocket formed on an inner surface thereof.

11. The protective composite fabric of claim 10, wherein the at least one pocket is operably able to receive and support a removable temperature adjustment element placed therein.

12. The protective composite fabric of claim 11, wherein the temperature adjustment element is a cooling layer.

13. The protective composite fabric of claim 10, wherein the at least one pocket comprises a plurality of pockets formed on the inner surface.

14. The protective composite fabric of claim 1, wherein the protective composite fabric is operable to prevent bodily penetration of a wearer as a result of stabbing or slashing from sharp objects or weapons.

15. The protective composite fabric of claim 1, further comprising cooling means interconnected with the protective composite fabric.

16. The protective composite fabric of claim 1, wherein the at least one second layer of ballistic and/or slash resistant fabric comprises a base layer having a polymer bonded thereto.

* * * * *